United States Patent
Fink et al.

(10) Patent No.: US 7,252,004 B2
(45) Date of Patent: Aug. 7, 2007

(54) IMAGING METHOD AND DEVICE EMPLOYING SHERAR WAVES

(75) Inventors: Mathias A. Fink, Meudon (FR); Mickael Tanter, Paris (FR)

(73) Assignees: Centre National de la Recherche Scientifique-CNRS, Paris Cedex (FR); Universite Paris 7, Paris Cedex (FR)

( * ) Notice: Subject to any disclaimer, the term of this patent is extended or adjusted under 35 U.S.C. 154(b) by 82 days.

(21) Appl. No.: 10/526,407

(22) PCT Filed: Aug. 12, 2003

(86) PCT No.: PCT/FR03/02516

§ 371 (c)(1),
(2), (4) Date: Mar. 2, 2005

(87) PCT Pub. No.: WO2004/021038

PCT Pub. Date: Mar. 11, 2004

(65) Prior Publication Data

US 2005/0252295 A1    Nov. 17, 2005

(30) Foreign Application Priority Data

Sep. 2, 2002    (FR) .................................. 02 10838

(51) Int. Cl.
*G01N 29/024* (2006.01)
*A61B 8/00* (2006.01)

(52) U.S. Cl. ............................ 73/597; 73/602; 73/626; 600/443; 600/587

(58) Field of Classification Search ................... 73/597, 73/602, 625, 626; 600/443, 438, 447, 587
See application file for complete search history.

(56) References Cited

U.S. PATENT DOCUMENTS

| 5,010,885 A | 4/1991 | Fink et al. |
| 5,178,147 A * | 1/1993 | Ophir et al. ................. 600/437 |
| 5,276,654 A | 1/1994 | Mallart et al. |

(Continued)

FOREIGN PATENT DOCUMENTS

FR    2 791 136    9/2000

(Continued)

OTHER PUBLICATIONS

Search Report for corresponding French Patent Application Serial No. FR 0210838, report dated May 15, 2003.

(Continued)

*Primary Examiner*—Hezron Williams
*Assistant Examiner*—Jacques M. Saint-Surin
(74) *Attorney, Agent, or Firm*—Marshall, Gerstein & Borun LLP

(57) ABSTRACT

An imaging method for observing the propagation of a shear wave simultaneously at a multitude of points in a diffusing viscoelastic medium. The shear wave is caused to be generated by firing at least one focused ultrasound compression wave into the viscoelastic medium by means of an array of transducers, and then emitting at a fast rate and using the same array of transducers, unfocused ultrasound compression waves serving to obtain a succession of images of the medium, and processing the images obtained in this way in deferred time in order to determine the movements of the medium during the propagation of the shear wave.

13 Claims, 1 Drawing Sheet

U.S. PATENT DOCUMENTS

| | | | |
|---|---|---|---|
| 5,487,387 | A | 1/1996 | Trahey et al. |
| 5,524,636 | A * | 6/1996 | Sarvazyan et al. ........... 600/587 |
| 5,606,971 | A | 3/1997 | Sarvazyan |
| 5,678,565 | A * | 10/1997 | Sarvazyan ................... 600/587 |
| 5,810,731 | A | 9/1998 | Sarvazyan et al. |
| 5,833,633 | A * | 11/1998 | Sarvazyan ................... 600/587 |
| 5,903,516 | A | 5/1999 | Greenleaf et al. |
| 5,922,961 | A * | 7/1999 | Hsu et al. ...................... 73/606 |
| 6,770,033 | B1 | 8/2004 | Fink et al. |
| 2004/0054282 | A1 | 3/2004 | Aubry et al. |

FOREIGN PATENT DOCUMENTS

| | | |
|---|---|---|
| FR | 2 815 717 | 4/2002 |
| WO | WO 00/55616 | 9/2000 |

OTHER PUBLICATIONS

International Search Report for corresponding PCT Patent Application Serial No. PCT/FR2003/002516.

Nightingale et al., "Acoustic Remote Palpation: Initial In Vivo Results", IEEE Ultrasonics Symposium, 6 pages (2000).

Nightingale et al., "On the Feasibility of Remote Palpation Using Acoustic Radiation Force", J. Acoust. Soc. Am., vol. 110, No. 1, pp. 625-634 (Jul. 2001).

Nightingale et al., "Acoustic Radiation Force Impulse Imaging: In Vivo Demonstration of Clinical Feasibility", Ultrasound in Medicine and Biology, vol. 28, No. 2, pp. 227-235 (Nov. 2, 2002).

Sandrin et al., "2D Transient Elastography", Acoustal Imaging, vol. 23, pp. 485-492 (2000).

Sandrin et al., "Time-Resolved Pulsed Elastography with Ultrafast Ultrasonic Imaging", Ultrasonic Imaging, vol. 21, pp. 259-272 (1999).

Sandrin et al., "Shear Modulus Imaging with 2-D Transient Elastography", IEEE Transactions on Ultrasonics, Ferroelectrics, and Frequency Control, vol. 49, No. 4, pp. 426-435 (Apr. 2002).

Sarvazyan et al., "Shear Wave Elasticity Imaging: A New Ultrasonic Technology of Medical Diagnostic", Ultrasound in Med. & Biol., vol. 24, No. 9, pp. 1419-1435 (Nov. 9, 1998).

* cited by examiner

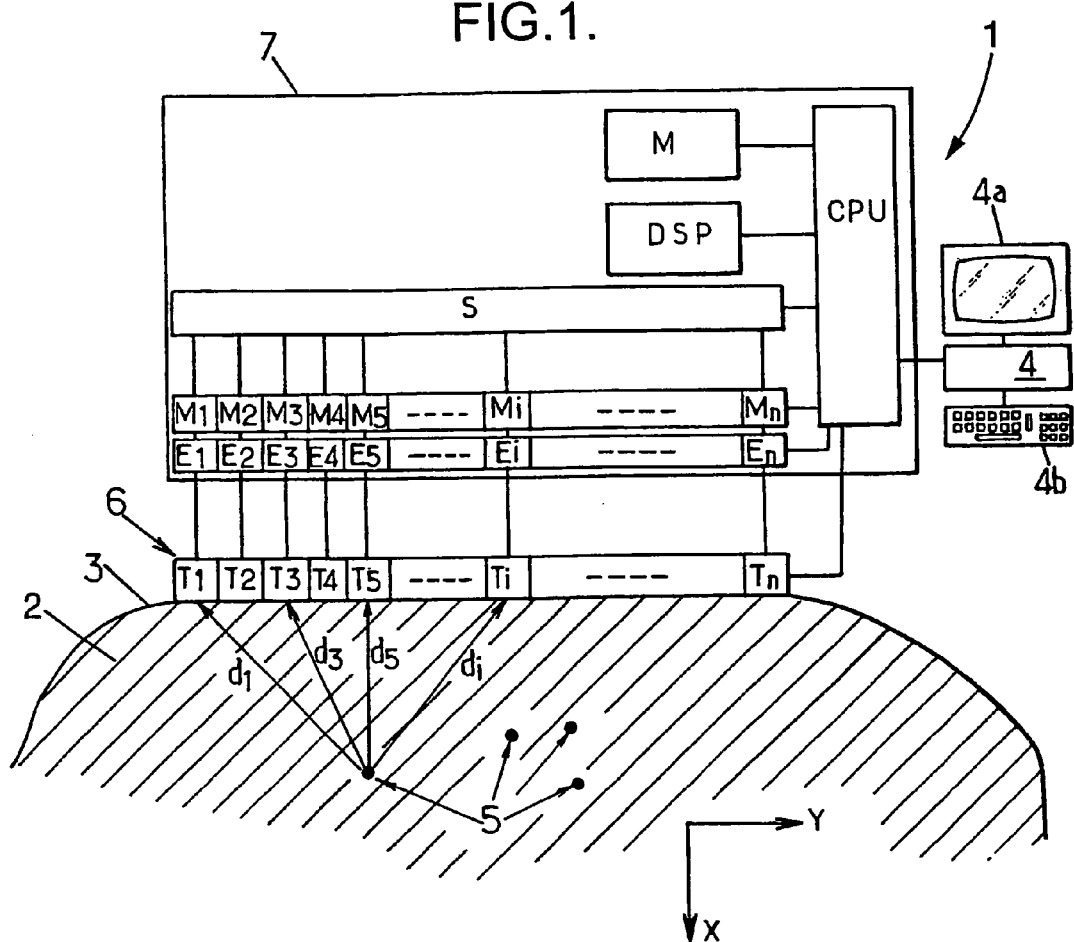

IMAGING METHOD AND DEVICE EMPLOYING SHERAR WAVES

FIELD OF THE DISCLOSURE

The present invention relates to imaging methods and apparatuses using shear waves.

BACKGROUND OF THE DISCLOSURE

More particularly, the invention relates to an imaging method using shear waves for observing a diffusing viscoelastic medium containing particles that reflect ultrasound compression waves, said method comprising:

a) an excitation step during which an elastic shear wave is generated in the viscoelastic medium;

b) an observation step during which the propagation of the shear wave is observed simultaneously at a multitude of points in an observation field in the viscoelastic medium, this observation step comprising the following substeps:

b1) causing an array of transducers that are controlled independently of one another to emit into the viscoelastic medium a succession of unfocused ultrasound compression wave shots at a rate of at least 500 shots per second; and b2) causing sound signals received from the viscoelastic medium to be detected and recorded in real time, said signals comprising the echoes generated by the unfocused ultrasound compression wave interacting with the reflecting particles in said viscoelastic medium; and c) at least one processing step during which:

c1) the sound signals received successively from the viscoelastic medium during substep b2) are processed in order to determine successive propagation images of the shear wave; and c2) at least one movement parameter of the viscoelastic medium is determined at different points of the observation field.

This produces a "motion picture" clearly illustrating the propagation of the shear wave through the viscoelastic medium, which can make it possible to perform qualitative and/or quantitative analysis in order to identify zones having hardness that differs from the hardness of the remainder of the viscoelastic medium, or zones having relaxation time that differs from the relaxation time of the remainder of the viscoelastic medium.

Document WO-A-00/55616 describes an example of such a method, in which shear waves are generated at the surface of the viscoelastic medium. That method gives full satisfaction in particular when imaging zones situated relatively close to the surface of the viscoelastic medium. However that known method does not enable certain zones to be observed in the viscoelastic medium, and in particular:

zones that are sufficiently deep to be unreachable by shear waves generated at the surface (shear waves attenuate quickly); and shadow zones that are masked by obstacles (in particular portions of a patient's skeleton or liquid zones such as liquid cysts) which impede the propagation of shear waves.

In addition, if the observation field is partially in a shadow zone, it can be necessary to move the shear wave generator device during an observation, which is tedious for the user.

Finally, the shear wave generator device is relatively heavy and complicates the apparatus.

SUMMARY OF THE DISCLOSURE

A particular object of the present invention is to mitigate those drawbacks.

To this end, according to the invention, a method of the kind in question is characterized in that during excitation step a) the elastic shear wave is caused to be generated by causing at least one focused ultrasound wave to be emitted into the viscoelastic medium by said array of transducers, the focusing and the timing of said focused ultrasound wave, and the timing of said unfocused ultrasound wave being adapted so that at least some of said unfocused ultrasound waves penetrate into the observation field while the shear wave is propagating in the observation field.

Thus, the same array of transducers can be used both for generating the elastic shear wave in selected manner in the observation field, and for subsequently observing said propagation by virtue of the fact that the imaging apparatus is adapted to generate either focused ultrasound waves enabling the elastic shear waves to be generated or unfocused ultrasound waves enabling the propagation of the shear wave to be observed, and suitably selecting:

the timing of the various emissions; and the point(s) on which the focused ultrasound wave is/are focused.

The imaging method of the invention is thus easy to implement for a user using apparatus that is relatively simple and lightweight. The invention is thus of very low cost compared with competing techniques such as magnetic resonance imaging (MRI), and where appropriate it makes it possible to establish outpatient imaging systems that can be used for preoperative imaging, postoperative imaging, and even for imaging while an operation is in progress.

By way of example, in medical applications, the method of the invention can make it possible for cancerous zones within the tissues of a patient to be identified effectively. Shear waves propagate through cancerous zones in very different manner than through adjacent zones. This identification can be performed much more easily than by conventional observation using simple ultrasound echography, since the propagation of shear waves is a function of the shear modulus of the medium, which is itself highly variable between zones of healthy tissue and a zone of cancerous tissue: typically, the shear modulus varies over a ratio of 1 to 30 between a healthy zone and a cancerous zone, whereas the compression modulus, which governs the propagation of compression soundwaves as used in ultrasound echography varies only by about 5% between healthy tissue and cancerous tissue.

Similarly, it is thus possible to identify zones of necrosis within tissue, for example tumor zones that have been subjected to ultrasound hyperthermia treatment, in particular for the purpose of evaluating the effectiveness of the hyperthermia treatment.

Another possible application of the invention relates to quantitatively evaluating the degree of fibrosis of the liver, which is an important parameter in liver disease, in particular hepatitis C.

It should be observed that the invention makes it possible to generate the shear wave, and to observe its propagation, including through a zone of liquid or through a bone barrier (skull, rib cage, etc.) completely or partially masking the observation field, since it is possible to focus ultrasound waves through such barriers (see in particular document WO-A-02/32316 or French patent application No. 02/10682 of Aug. 28, 2002).

In preferred implementations of the method of the invention, it is optionally possible also to have recourse to one or more of the following dispositions:

during substep b2), in order to determine said movement parameter, a plurality of successive propagation images (e.g. by correlation, Doppler, etc.) are compared with a common reference image of the viscoelastic medium, the reference image being determined by firing at least one unfocused ultrasound compression wave into said viscoelastic medium and then detecting and recording echoes generated by said unfocused ultrasound compression wave on interacting with the reflecting particles in the viscoelastic medium (thus improving the accuracy with which the movement parameter is measured (e.g. displacement) in the viscoelastic medium, in particular for movement of small amplitude (typically less than 30 micrometers ($\mu$m) with the soundwave excitation technique used herein));

step a) is preceded by an initial observation step a0) during which at least one unfocused ultrasound compression wave is fired and then echoes generated by said unfocused ultrasound compression wave interacting with the reflecting particles in the viscoelastic medium are detected and recorded, said echoes corresponding (directly or indirectly) to an initial image of the viscoelastic medium, and during substep b2), said initial image constitutes said reference image for processing at least some of the successive displacement images;

during initial observation step a0), a plurality of unfocused ultrasound compression waves are fired in succession and then echoes generated by each unfocused ultrasound compression wave interacting with the reflecting particles of the viscoelastic medium are detected and recorded, said echoes corresponding (directly or indirectly) to a plurality of successive images of the viscoelastic medium, and said initial image of the viscoelastic medium is determined by combining said successive images;

said movement parameter is a displacement of the viscoelastic medium;

the focused ultrasound wave emitted during excitation step a) presents a frequency f lying in the range 0.5 megahertz (MHz) to 15 MHz, and is emitted for a duration of k/f seconds, where k is an integer lying in the range 50 to 5000 and f is expressed in hertz (Hz);

the focused ultrasound wave emitted during excitation step a) presents a frequency lying in the range 0.5 MHz to 15 MHz and is emitted during a succession of emission periods separated by rest periods, the emission periods following one another at a rate lying in the range 10 to 1000 emissions per second;

the focused ultrasound wave emitted during excitation step a) is a linear combination (in particular a sum) of two monochromatic signals having respective frequencies f1 and f2 such that 20 Hz$\leq$|f1−f2|$\leq$1000 Hz;

the focused ultrasound wave emitted during excitation step a) is focused simultaneously on a plurality of points;

image processing step c) is followed (immediately or otherwise) by a mapping step d) during which, on the basis of variation in the movement parameter over time, at least one shear wave propagation parameter is calculated at at least some points of the observation field in order to determine a map of said propagation parameter in the observation field;

the shear wave propagation parameter which is calculated during mapping step d) is selected from shear. wave speed, shear modulus, Young's modulus, shear wave attenuation, shear elasticity, shear viscosity, and mechanical relaxation time; and steps a) to d) are repeated successively while emitting different focused ultrasound waves during successive excitation step a), and then combining the maps obtained during the successive mapping step d) in order to calculate a combination map of the observation field.

Furthermore, the invention also provides an imaging apparatus for implementing a method according to any preceding claim using shear waves to observe a diffusing viscoelastic medium containing particles that reflect ultrasound compression waves, the apparatus comprising an array of transducers that are controlled independently of one another by at least one electronic central unit adapted:

to cause at least one elastic shear wave to be generated in the viscoelastic medium;

to observe the propagation of the shear wave simultaneously at a multitude of points in an observation field in the viscoelastic medium by causing said array of transducers to emit into the viscoelastic medium a succession of unfocused ultrasound compression wave shots at a rate of at least 500 shots per second, then causing said array of transducers to detect in real time and record in real time sound signals received from the viscoelastic medium, the sound signals comprising the echoes generated by the unfocused ultrasound compression wave interacting with the reflecting particles of said viscoelastic medium; and processing the successive sound signals received from the viscoelastic medium to determine successive propagation images of the shear wave, and then determining at least one movement parameter of the viscoelastic medium at different points of the observation field; the apparatus being characterized in that the electronic central unit is adapted to cause the elastic shear wave to be generated by causing at least one focused ultrasound wave to be emitted into the viscoelastic medium by said array of transducers, the focusing and the timing of said focused ultrasound wave, and the timing of said unfocused ultrasound wave being adapted so that said unfocused ultrasound waves reach the observation field during the propagation of the shear wave through the observation field.

BRIEF DESCRIPTION OF THE DRAWINGS

Other characteristics and advantages of the invention appear from the following description of an embodiment thereof, given by way of non-limiting example and with reference to the accompanying drawing.

In the drawing, FIG. 1 is a diagrammatic view of a shear-wave imaging device in an embodiment of the invention.

DETAILED DESCRIPTION

The imaging device 1 shown in FIG. 1 is for studying the propagation of elastic shear waves in a viscoelastic medium 2 that diffuses ultrasound waves in compression, and that may be constituted, for example:

by an inert body, in particular for quality control in industrial applications; or a living body, for example a portion of the body of a patient, in medical applications.

By way of example, these movements are tracked by means of a microcomputer 4 (comprising at least an input interface 4a such as a keyboard, etc., and an output interface such as a screen, etc.) or any other electronic central unit, serving to send ultrasound compression waves into the medium 2 from its outside surface 3, which waves interact with diffusing particles 5 contained in the medium 1, which particles are reflective for ultrasound compression waves. The particles 5 may be constituted by any non-uniformity in the medium 1, and in particular, in a medical application, they may be constituted by particles of collagen present in human tissues (in echographic images, such particles form points known as "speckle").

To observe the propagation of the shear wave, an ultrasound probe 6 is used that is disposed against the outside surface 3 of the observed medium 1. This probe delivers ultrasound compression wave pulses along an axis X, which pulses are of the type commonly used in echography, for example having a frequency lying in the range 0.5 MHz to 100 MHz, and preferably in the range 0.5 MHz to 15 MHz, e.g. being about 4 MHz.

The ultrasound probe 6 is constituted by an array of $n$ ultrasound transducers T1, T2, ..., Ti, Tn, where $n$ is an integer not less than 1.

By way of example, the probe 6 may be in the form of a linear strip capable of comprising, for example, n=128 transducers in alignment along an axis Y that is perpendicular to the axis X. However, the probe in question could equally be in the form of a two-dimensional array of transducers (plane or otherwise).

The transducers T1, T2, ..., Tn are controlled independently of one another by the microcomputer 4, possibly via a central unit CPU which is contained for example in an electronics rack 7 connected via a flexible cable to the probe 6. The transducers T1-Tn can thus emit selectively:

either an ultrasound compression wave that is "plane" (i.e. a wave whose wave front is rectilinear in the X,Y plane), or any other type of unfocused wave illuminating the entire observation field in the medium 2, for example a wave generated by causing random sound signals to be emitted by the various transducers T1-Tn;

or else an ultrasound compression wave that is focused on one or more points of the medium 2.

To observe the propagation of the shear wave in the medium 2, several steps are performed in succession:

a) an excitation step during which the microcomputer 4 causes an elastic shear wave to be generated in the viscoelastic medium 2 by causing at least one ultrasound wave that is focused in the viscoelastic medium to be emitted by the probe 6;

b) an observation step during which the propagation of the shear wave is observed simultaneously at a multitude of observation field points in the viscoelastic medium 2, this observation step comprising the following substeps:

b1) the microcomputer 4 causes the probe 6 to emit into the viscoelastic medium a succession of unfocused ultrasound compression wave shocks at a rate of at least 500 shots per second (the focusing and the timing of the focus ultrasound wave emitted in step a), and the timing of said unfocused ultrasound wave are adapted so that at least some of said unfocused ultrasound waves reach the observation field during the propagation of the shear wave through the observation field, for at least some of the unfocused ultrasound wave emissions;

b2) the microcomputer 4 causes the probe 6 to detect and record in real time sound signals received from the viscoelastic medium 2, said signals comprising echoes generated by the unfocused ultrasound compression wave interacting with the reflecting particles 5 in the viscoelastic medium, these echoes corresponding (directly or indirectly) to successive images of the displacement of the viscoelastic medium;

c) and at least one processing step during which:

c1) the microcomputer 4 processes the successive sound signals received from the viscoelastic medium 2 during substep b2) in order to determine successive propagation images; and c2) the microcomputer 4 determines at least one movement parameter for the viscoelastic medium 2 at various points in the observation field.

The focused ultrasound wave emitted during the excitation step a) may be a monochromatic wave of frequency $f$ lying in the range 0.5 MHz to 15 MHz, for example being equal to about 4 MHz, which is emitted for a duration of k/f seconds, where $k$ is an integer lying in the range 50 to 5000 (e.g. being about 500) and $f$ is expressed in Hz. Such a wave may possibly be emitted during a succession of emission periods separated by rest periods, the emission periods following one another at a rate lying in the range 10 to 1000 emissions per second.

In a variant, the focused ultrasound wave emitted during excitation step a) is a linear combination (in particular a sum) of two monochromatic signals of respective frequencies f1 and f2 such that 20 Hz≦|f1−f2|≦1000 Hz, thus producing an amplitude modulated wave having a modulation frequency |f1−f2|.

In addition, the focused ultrasound wave emitted during excitation step a) may optionally be focused simultaneously or otherwise on a plurality of points so that the shear wave as generated presents a desired wave shape (for example it is thus possible to generate a shear wave that is plane, or on the contrary a shear wave that is focused) and illuminates desired zones in the. medium 2.

During step b1), which may last for example for less than one second, it is possible to emit unfocused ultrasound compression waves at a rate lying in the range 500 to 10,000 shots per second, and preferably in the range 1000 to 5000 shots per second (with this rate being limited by the go-and-return travel time for the compression wave through the medium 2, i.e. by the thickness of the medium 2 in the direction X: it is necessary for all of the echoes that are generated by the compression wave to have been received by the probe 6 before a new compression wave is sent).

Each unfocused ultrasound compression wave propagates through the medium 2 at a propagation speed that is much higher than that of shear waves (e.g. about 1500 meters per second (m/s) in the human body), and interacts with the reflecting particles 5, thereby generating echoes or other analogous disturbances in the signal that are known in themselves under the name "speckle noise" in the field of echography.

The speckle noise is picked up by the transducers T1, ..., Tn during substep b2), after each shot of an unfocused ultrasound compression wave. The signal sij(t) as picked up in this way by each transducer Ti after shot No. $j$ is initially sampled at high frequency (e.g. 30 MHz to 100 MHz) and is digitized in real time (e.g. on 12 bits) by a sampler forming part of the rack 7 and connected to said transducer, the samplers being referenced respectively E1, E2, ..., En.

The signal sij(t) as sampled and digitized in this way is then stored, likewise in real time, in a memory Mi belonging to the rack 7 and specific to the transducer Ti.

By way of example, each memory Mi presents a capacity of about 128 megabytes (MB), and contains all of the signals sij(t) received in succession for shots j=1 to p.

In deferred time, after all of the signals sij(t) corresponding to the same propagation of a shear wave have been stored, the central unit CPU causes these signals to be reprocessed by a summing circuit S belonging to the rack 7 (or else it performs this treatment itself, or indeed the treatment may be performed in the microcomputer 4), using a conventional path-forming step corresponding to substep c1).

This generates signals Sj(x,y) each corresponding to the image of the observation field after shot No. j (when the unfocused ultrasound wave is a plane wave).

For example, it is possible to determine a signal Sj(t) by the following formula:

$$Sj(t) = \sum_{i=1}^{n} \alpha_i(x, y) \cdot sij[t(x, y) + d_i(x, y)/V]$$

where:

sij is the raw signal perceived by the transducer No. i after ultrasound compression wave shot No. j;

t(x,y) is the time taken by the ultrasound compression wave to reach the point of the observation field having coordinates (x,y), with t=0 at the beginning of shot No. j;

$d_i(x,y)$ is the distance between the point of the observation field having coordinates (x,y) and transducer No. i, or an approximation to said distance;

V is the mean propagation speed of ultrasound compression waves in the viscoelastic medium under observation; and $\alpha_i(x,y)$ is a weighting coefficient taking account of apodization relationships (in practice, in numerous cases, it is possible to assume that $\alpha_i(x,y)=1$).

The above formula applies mutatis mutandis when the observation field is three-dimensional (with a two-dimensional array of transducers), with space coordinates (x,y) being replaced by (x,y,z).

After the optional path-forming step, the central unit CPU stores in a central memory M forming part of the rack 7, the image signals Sj(x,y), or Sj(x), or Sj(x,y,z), each corresponding to shot No. j. These signals may also be stored in the microcomputer 4 if it is the microcomputer that performs the image processing itself.

These images are then processed in deferred time in substep c2) by correlation and advantageously by cross-correlation either in pairs, or preferably with a reference image which may be:

either a displacement image determined previously as explained above and used as a reference image for subsequent displacement images (or for a limited number of subsequent displacement images), e.g. 30 displacement images);

or else determined during a preliminary initial observation step a0), like the above-mentioned successive displacement images, by causing one or more unfocused ultrasound waves to be emitted by the probe 6 before excitation step a) which generates the shear wave (when a plurality of unfocused ultrasound compression waves are emitted in this way prior to the excitation stage, echoes generated by each unfocused compressed ultrasound wave are recorded interacting with the reflecting particles in the viscoelastic medium, these echoes corresponding to a plurality of successive preliminary images of the viscoelastic medium, and said initial image of the viscoelastic medium is determined by combining said successive preliminary images, and in particular by averaging the pixel values of said preliminary images).

The above-mentioned cross-correlation can be performed, for example, in a specialized digital signal processor (DSP) electronic circuit belonging to the rack 7, or it may be programmed in the central unit CPU or in the microcomputer 4.

During this cross-correlation process, a cross-correlation function <Sj(x,y),Sj+1(x,y)> is maximized in order to determine the displacement to which each particle 5 giving rise to an ultrasound echo has been subjected.

Examples of such cross-correlation calculations are given in the state of the art, in particular by O'Donnell et al. in "Internal displacement and strain imaging using speckle tracking", IEEE transactions on ultrasound, ferroelectrics, and frequency control, Vol. 41, No. 3, May 1994, pp. 314-325, and by Ophir et al. in "Elastography: a quantitative method for imaging the elasticity of biological tissues", Ultrasound Imag., Vol. 13, pp. 111-134, 1991.

This produces a set of displacement vectors $\bar{u}(\bar{r}, t)$ generated by the shear waves in each position $\bar{r}$ of the medium 2 under the effect of the shear wave (these displacement vectors may optionally be reduced to a single component in the example described herein).

This set of displacement vectors is stored in the memory M or in the microcomputer 4 and can be displayed, for example, in particular by means of the screen 4a of the computer, in the form of a slow motion picture in which the values of the displacements are illustrated by an optical parameter such as a gray level or a color level.

The propagation differences of the shear wave between zones having different characteristics in the medium 2 can thus be seen clearly, for example the zones may comprise healthy tissue and cancerous tissue in a medical application.

The motion picture of shear wave propagation can also be superposed on a conventional echographic image, which can also be generated by the apparatus 1 described above.

Furthermore, it is also possible to calculate not the displacements of each of the points in the observed medium 2, but the deformations of the medium 2, i.e. vectors whose components are the derivatives of the displacement vectors respectively relative to the space variables (X and Y coordinates in the example described). These deformation vectors can be used like the displacement vectors for clearly viewing the propagation of the shear wave in the form of a motion picture, and they also present the advantage of eliminating displacements of the probe 6 relative to the medium 2 under observation.

From the displacement or deformation fields, the microcomputer 4 can advantageously then proceed with a map-making step d) during which, on the basis of the way in which the movement parameter (displacement or deformation) varies over time in the field of observation X, Y (or X, Y, Z with a two-dimensional array of transducers), it calculates at least one propagation parameter of the shear wave, either at certain points in the observation field as selected by the user acting on the microcomputer 4, or else throughout the observation field.

The propagation parameter of the shear wave that is calculated during the map-making step is selected, for example, from amongst: the propagation speed $c_s$ of shear waves, the shear modulus $\mu$, or Young's modulus $E=3\mu$, the attenuation $\alpha$ of the shear waves, the shear elasticity $\mu 1$, the shear viscosity $\mu 2$, or the mechanical relaxation time $\tau_s$ of the tissues.

For example, it is possible at various points in the observation field to calculate:

the value of the propagation speed $c_s$ of the shear wave, thus giving information about the hardness of the tissues;

the value of the mechanical relaxation time $\tau_s$ of the tissues, which is characteristic of the local viscosity of the medium.

To do this, the following propagation equation (1) is used, with the displacement $\overline{u}(\overline{r}, t)$ generated by the shear waves at each position $\overline{r}$ of the medium satisfying this equation:

$$\rho \frac{\partial^2 p\overline{u}(\overline{r}, t)}{\partial t^2} = c_s^2 \left(1 + \tau_s \frac{\partial}{\partial t}\right) \cdot \overline{\nabla}^2 \overline{u}(\overline{r}, t) \quad (1)$$

where $\rho$ is the density of the tissues, $\tau_s$ is the mechanical relaxation time of the tissues, and $c_s$ is the propagation speed of the shear wave which is directly related to Young's modulus E of the tissue by the following relationship:

$$c_s = \sqrt{\frac{E}{3\rho}} \quad (2)$$

In the Fourier domain, the above wave equation (1) can be written as follows:

$$\omega^2 \rho U(\overline{r},\omega) = c_s^2(1+j\omega\tau).\Delta U(\overline{r},\omega) \quad (3)$$

where $U(\overline{r},\omega)$ is the Fourier transform of the displacement field $\overline{u}(\overline{r},t)$ measured at each point, and $\Delta U(\overline{r},\omega)$ is the Fourier transform of the spatial Laplacian of the field $\overline{u}(\overline{r},t)$. Given that $\omega\tau_s \ll 1$, it is possible to use a simplified expression:

$$c_s^2 = \omega^2 \rho \frac{U(\overline{r}, \omega)}{\Delta U(\overline{r}, \omega)} \quad (4)$$

$$\tau_s = \frac{1}{\omega}\tan\left(\psi\left(\frac{U(\overline{r}, \omega)}{\Delta U(\overline{r}, \omega)}\right)\right) \quad (5)$$

where $\psi(x)$ is the phase of the complex variable $x$. The functions $U(\overline{r},\omega)$ and $\Delta U(\overline{r},\omega)$ are known for each point of the echographic image, so it is possible to measure Young's modulus and the mechanical relaxation time of the tissue at each point in the space, thereby drawing up a map of those two parameters.

Since equations (4) and (5) are true at each frequency, the calculation of $c_s$ and $\tau_s$ can advantageously be averaged over the entire band of frequencies carried by the shear wave, thereby greatly improving the quality of the mapping that is performed. For this purpose, it is possible to use the following formulae:

$$c_s^2 = \frac{1}{\omega_1 - \omega_0} \int_{\omega_0}^{\omega_1} \omega^2 \rho \frac{U(\overline{r}, \omega)}{\Delta U(\overline{r}, \omega)} d\omega \quad (6)$$

$$\tau_s = \frac{1}{\omega_1 - \omega_0} \int_{\omega_0}^{\omega_1} \frac{1}{\omega}\tan\left(\psi\left(\frac{U(\overline{r}, \omega)}{\Delta U(\overline{r}, \omega)}\right)\right) d\omega \quad (7)$$

where $\omega_0$ and $\omega_1$ are the minim and maximum frequencies carried by the shear wave.

The method of calculation would be the same when using not displacements but deformations in the observed medium 2.

Furthermore, it is advantageous to establish a succession of several maps of the desired propagation parameters, e.g. $c_s$ and $\tau_s$, by generating successive different shear waves, e.g. obtained by emitting ultrasound compression waves focused successively on a plurality of points or having different wave shapes. It is then possible to combine the various maps that are obtained in this way, e.g. by averaging them, so as to obtain a combination map that is richer and more accurate.

The invention claimed is:

1. An imaging method using shear waves for observing a diffusing viscoelastic medium containing particles that reflect ultrasound compression waves, said method comprising:
   a) an excitation step during which an elastic shear wave is generated in the viscoelastic medium;
   b) an observation step during which the propagation of the shear wave is observed simultaneously at a multitude of points in an observation field in the viscoelastic medium, this observation step comprising the following substeps:
      b1) causing an array of transducers that are controlled independently of one another to emit into the viscoelastic medium a succession of unfocused ultrasound compression wave shots at a rate of at least 500 shots per second; and
      b2) causing sound signals received from the viscoelastic medium to be detected and recorded in real time, said signals comprising the echoes generated by the unfocused ultrasound compression wave interacting with the reflecting particles in said viscoelastic medium; and
   c) at least one processing step during which:
      c1) the sound signals received successively from the viscoelastic medium during substep b2) are processed in order to determine successive propagation images of the shear wave; and
      c2) at least one movement parameter of the viscoelastic medium is determined at different points of the observation field;
   the method further comprising:
   during the excitation step a) the elastic shear wave is caused to be generated by causing at least one focused ultrasound wave to be emitted into the viscoelastic medium by said array of transducers, the focusing and the timing of said focused ultrasound wave, and the timing of said unfocused ultrasound wave being adapted so that at least some of said unfocused ultrasound waves penetrate into the observation field while the shear wave is propagating in the observation field, for at least some of the unfocused ultrasound wave emissions.

2. A method according to claim 1, in which during substep b2), in order to determine said movement parameter, plurality of successive propagation images are compared with a common reference image of the viscoelastic medium, the reference image being determined by firing at least one unfocused ultrasound compression wave into said viscoelastic medium and then detecting and recording echoes generated by said unfocused ultrasound compression wave on interacting with the reflecting particles in the viscoelastic medium.

3. A method according to claim 2, in which step a) is preceded by an initial observation step a0) during which at least one unfocused ultrasound compression wave is fired and then echoes generated by said unfocused ultrasound compression wave interacting with the reflecting particles in the viscoelastic medium are detected and recorded, said echoes corresponding to an initial image of the viscoelastic medium, and during substep b2), said initial image constitutes said reference image for processing at least some of the successive displacement images.

4. A method according to claim 3, in which, during initial observation step a0), a plurality of unfocused ultrasound compression waves are fired in succession and then echoes generated by each unfocused ultrasound compression wave interacting with the reflecting particles of the viscoelastic medium are detected and recorded, said echoes corresponding to a plurality of successive images of the viscoelastic medium, and said initial image of the viscoelastic medium is determined by combining said successive images.

5. A method according to claim 1, in which said movement parameter is a displacement of the viscoelastic medium.

6. A method according to claim 1, in which the focused ultrasound wave emitted during excitation step a) presents a frequency flying in the range 0.5 MHz to 15 MHz, and is emitted for a duration of k/f seconds, where k is an integer lying in the range 50 to 5000 and f is expressed in Hz.

7. A method according to claim 1, in which the focused ultrasound wave emitted during excitation step a) presents a frequency lying in the range 0.5 MHz to 15 MHz and is emitted during a succession of emission periods separated by rest periods, the emission periods following one another at a rate lying in the range 10 to 1000 emissions per second.

8. A method according to claim 1, in which the focused ultrasound wave emitted during excitation step a) is a linear combination (in particular a sum) of two monochromatic signals having respective frequencies f1 and f2 such that 20 Hz≤|f1−f2|≤1000 Hz.

9. A method according to claim 1, in which the focused ultrasound wave emitted during excitation step a) is focused simultaneously on a plurality of points.

10. A method according to claim 1, in which image processing step c) is followed by a mapping step d) during which, on the basis of variation in the movement parameter over time, at least one shear wave propagation parameter is calculated at at least some points of the observation field in order to determine a map of said propagation parameter in the observation field.

11. A method according to claim 1, in which the shear wave propagation parameter which is calculated during mapping step d) is selected from shear wave speed, shear modulus, Young's modulus, shear wave attenuation, shear elasticity, shear viscosity, and mechanical relaxation time.

12. A method according to claim 11, in which steps a) to d) are repeated successively while emitting different focused ultrasound waves during successive excitation step a), and then combining the maps obtained during the successive mapping step d) in order to calculate a combination map of the observation field.

13. Imaging apparatus for implementing a method according to claim 1 using shear waves to observe a diffusing viscoelastic medium containing particles that reflect ultrasound compression waves, the apparatus comprising an array of transducers that are controlled independently of one another by at least one electronic central unit adapted:

to cause at least one elastic shear wave to be generated in the viscoelastic medium;

to observe the propagation of the shear wave simultaneously at a multitude of points in an observation field in the viscoelastic medium by causing said array of transducers to emit into the viscoelastic medium a succession of unfocused ultrasound compression wave shots at a rate of at least 500 shots per second, then causing said array of transducers to detect in real time and to record in real time sound signals received from the viscoelastic medium, the sound signals comprising the echoes generated by the unfocused ultrasound compression wave interacting with the reflecting particles of said viscoelastic medium; and processing the successive sound signals received from the viscoelastic medium to determine successive propagation images of the shear wave, and then determinine at least one movement parameter of the viscoelastic medium at different points of the observation field;

and further wherein the electronic central unit is adapted to cause the elastic shear wave to be generated by causing at least one focused ultrasound wave to be emitted into the viscoelastic medium by said array of transducers, the focusing and the timing of said focused ultrasound wave, and the timing of said unfocused ultrasound wave being adapted so that said unfocused ultrasound waves reach the observation field during the propagation of the shear wave through the observation field.

* * * * *